United States Patent [19]

Tomioka et al.

[11] 3,966,720

[45] June 29, 1976

[54] PROCESS FOR PRODUCING DESACETOXY CEPHALOSPORANIC ACID COMPOUND

[75] Inventors: Tatsuo Tomioka, Tokyo; Yasuo Hoshide, Okegawa; Hirosi Ogawa, Ageo; Kenichi Suzuki, Funabashi, all of Japan

[73] Assignee: Nikken Chemicals Co., Ltd., Tokyo, Japan

[22] Filed: Dec. 10, 1973

[21] Appl. No.: 423,187

[30] Foreign Application Priority Data

Dec. 9, 1972 Japan................ 47-123830
Dec. 12, 1972 Japan................ 47-125958
Dec. 27, 1972 Japan................ 48-1594
Mar. 9, 1973 Japan................ 48-27729

[52] U.S. Cl. ................. 260/243 C; 260/239.1
[51] Int. Cl.² ........................... C07D 501/10
[58] Field of Search ................... 260/243 C

[56] References Cited
UNITED STATES PATENTS

| | | | |
|---|---|---|---|
| 3,668,201 | 6/1972 | Gutowski............... | 260/243 C |
| 3,668,202 | 6/1972 | Foster et al............ | 260/243 C |
| 3,725,397 | 4/1973 | Graham et al.......... | 260/243 C |
| 3,725,399 | 4/1973 | Ellerton et al.......... | 260/243 C |
| 3,843,637 | 10/1974 | Rubinfeld et al........ | 260/243 C |
| 3,852,281 | 12/1974 | Verweij................. | 260/243 C |
| 3,852,295 | 12/1974 | Graham et al.......... | 260/243 C |

*Primary Examiner*—Nicholas S. Rizzo
*Attorney, Agent, or Firm*—Oblon, Fisher, Spivak, McClelland & Maier

[57] ABSTRACT

A process for producing a desacetoxy cephalosporanic acid represented by formula (III),

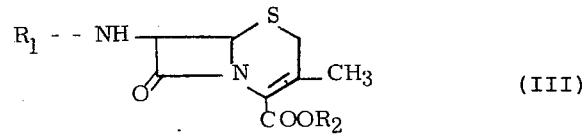

wherein $R_1$ is acyl, and $R_2$ is alkyl, aryl or arylalkyl, which comprises: heating a penicillin sulfoxide of the formula (I),

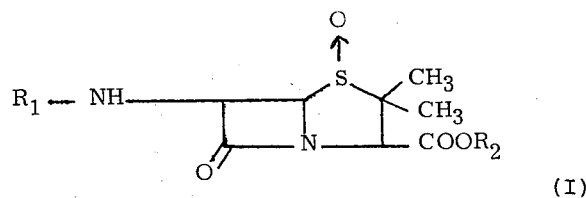

wherein $R_1$ and $R_2$ are the same as hereinbefore defined at 50° to 160°C in an inert organic solvent in the presence of a sulfonate represented by formula (II),

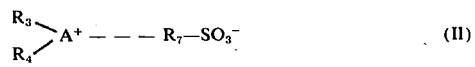

wherein A is $R_5$—N—$R_6$, $R_5$—N—O—$R_6$, S—$R_6$, $R_5$—S → O, and $R_3$, $R_4$, $R_5$ and $R_6$ are lower alkyl, phenyl, benzyl or phenethyl, $R_7$ is 1-12C alkyl, phenyl, 1-12C alkyl-substituted-phenyl, naphthyl, 1-12C alkyl-substituted naphthyl, halogen-substituted phenyl and wherein when A is $R_5$—N—$R_6$ or $R_5$—N—O—$R_6$, $R_3$, $R_4$ and $R_5$ may form a heterocyclic ring together with the nitrogen atom, and when A is S—$R_6$, $R_3$ and $R_4$ may form a heterocyclic 4-5C polymethylene ring or $R_6$ and $R_7$ may bond to form a polymethylene link.

14 Claims, No Drawings

PROCESS FOR PRODUCING DESACETOXY CEPHALOSPORANIC ACID COMPOUND

BACKGROUND OF THE INVENTION

1. Field of the Invention

The present invention relates to a process for converting penicillin sulfoxides to desacetoxy cephalosporanic acids. More particularly, the present invention relates to a process for producing 7-substituted aminodesacetoxy cephalosporanic acids represented by the formula (III)

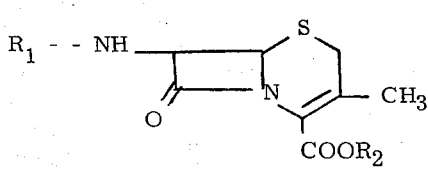
(III)

wherein $R_1$ is an acyl group, and $R_2$ is alkyl, aryl or arylalkyl which comprises heating penicillin sulfoxides represented by the formula (I),

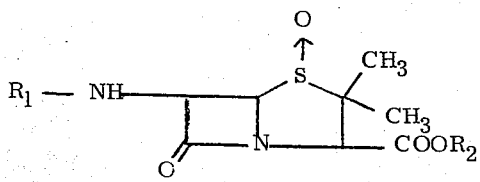
(I)

wherein $R_1$ and $R_2$ are the same as defined above, at 50° to 160°C in an inert organic solvent in the presence of a sulfonate represented by the formula (II), $$R_3\!\!>\!\!A^+ - - - R_7\!-\!SO_3^-  \quad (II)$$
$$R_4\!\!\nearrow$$

wherein A is

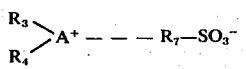

$S - R_6$ or

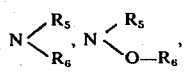

, and $R_3$, $R_4$, $R_5$ and $R_6$ are lower alkyl, phenyl, benzyl or phenethyl, $R_7$ is 1-12C alkyl, phenyl, 1-12C alkyl-substituted phenyl, naphthyl, 1-12C alkyl-substituted naphthyl, halogen-substituted phenyl, and wherein when A is

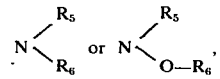

$R_3$, $R_4$ and $R_5$ may form a heterocyclic ring together with the nitrogen atom, and when A is $S-R_6$, $R_3$ and $R_4$ may form a heterocyclic 4-5C polymethylene ring or $R_6$ and $R_7$ may bond to form a polymethylene link.

2. Description of the Prior Art

The desacetoxy cephalosporanic acids represented by the formula (III) have antibacterial activity in themselves and are utilized in medicinal applications. However, the cephalosporanic acids are also useful as intermediates for the syntheses of other cephalosporin compounds having high antibacterial activity.

U.S. Pat. No. 3,275,626 discloses the conversion of 6-amino-penicillin sulfoxides to desacetoxy cephalosporanic acids upon heating at approximately 80° to 175°C under acidic conditions. This reaction is promoted by acetic anhydride or p-toluenesulfonic acid. However, in this process the reaction is conducted under severe conditions by heating the acids in acidic media. Thus, side reaction tends to readily occur resulting in low yields of product and poor economy.

A need, therefore, continues to exist for a process for converting penicillin sulfoxides in high yield and selectivity to aminodesacetoxy cephalosporanic acids.

SUMMARY OF THE INVENTION

Accordingly, one object of the present invention is to provide a process for converting 6-substituted aminopenicillin sulfoxides to 7-substituted aminodesacetoxy cephalosporanic acids.

Another object of the present invention is to provide a process for economically producing desacetoxy cephalosporanic acids.

Still another object of the present invention is to provide a heretofore unknown compound which promotes the conversion process.

Briefly, these objects and other objects of the invention as hereinafter will become more readily apparent can be attained by a process for producing a desacetoxy cephalosporanic acid represented by formula (III),

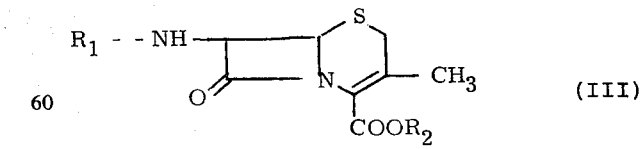
(III)

wherein $R_1$ is acyl, and $R_2$ is alkyl, aryl or arylalkyl, which comprises: heating a penicillin sulfoxide of the formula (I),

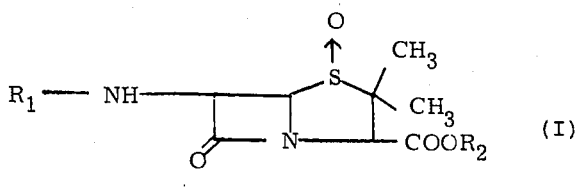

(I)

wherein $R_1$ and $R_2$ are the same as hereinbefore defined, at 50° to 160°C in an inert organic solvent in the presence of a sulfonate represented by formula (II),

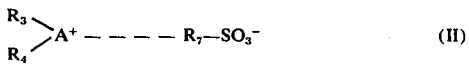

(II)

wherein A is $R_5$—N—$R_6$, $R_5$—N—O—$R_6$, S—$R_6$, $R_5$—S → O, and $R_3$, $R_4$, $R_5$ and $R_6$ are lower alkyl, phenyl, benzyl or phenethyl, $R_7$ is 1-12C alkyl, phenyl, 1-12C alkyl-substituted-phenyl, naphthyl, 1-12C alkyl-substituted naphthyl, halogen-substituted phenyl, and wherein when A is $R_5$—N—$R_6$ or $R_5$—N—O—$R_6$, $R_3$, $R_4$ and $R_5$ may form a heterocyclic ring together with the nitrogen atom, and when A is S—$R_6$, $R_3$ and $R_4$ may form a heterocyclic 4-5C polymethylene ring or $R_6$ and $R_7$ may bond to form a polymethylene link.

DESCRIPTION OF THE PREFERRED EMBODIMENTS

In the present invention, the desacetoxy cephalosporanic acids represented by formula (III) are most advantageously produced by heating the penicillin sulfoxides represented by formula (I) in the presence of 0.1 to 4 mole of a sulfonate of a quaternary ammonium salt represented by formula (IV),

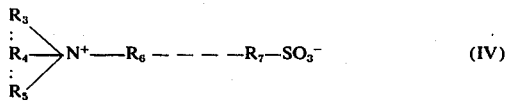

(IV)

wherein $R_3$, $R_4$, $R_5$, $R_6$ and $R_7$ are the same as hereinbefore defined, per one mole of the penicillin sulfoxides at 80° to 130°C preferably 90° to 115°C for over 1 hour in an inert organic solvent such as 1,4-dioxane, methyl isobutyl ketone, 1,2-dichloropropane, 1,1,2-trichloroethane.

In another embodiment of the present invention, the desacetoxy cephalosporanic acids represented by formula (III) are most advantageously produced by heating penicillin sulfoxides represented by the formula (I) in the presence of 0.1 to 4 mole of a sulfonate represented by formula (V),

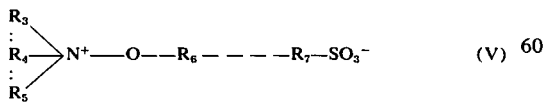

(V)

wherein $R_3$, $R_4$, $R_5$, $R_6$ and $R_7$ are the same as hereinbefore defined per one mole of the penicillin sulfoxides at 80° to 130°C, preferably 90° to 115°C, for over 30 minutes in one of the aforementioned inert organic solvents.

In yet another embodiment of the present invention, desacetoxy cephalosporanic acids represented by the formula (III) are preferably produced by heating the penicillin sulfoxides represented by formula (I) in the presence of 0.1 to 4.0 mole, preferably 0.5 to 4 mole of a sulfonate of a sulfonium compound represented by formula (VI)

(VI)

wherein $R_3$, $R_4$, $R_6$ and $R_7$ are the same as hereinbefore defined per one mole of the penicillin sulfoxide at 80° to 130°C, preferably 90° to 115°C for over one hour in one of the aforementioned inert organic solvents.

In still another embodiment of the present invention, the desacetoxy cephalosporanic acids represented by the formula (III) are most advantageously produced by heating the penicillin sulfoxides represented by the formula (I) in the presence of 0.2 to 4 mole, preferably 0.5 to 4 mole of a sulfoxonium sulfonate represented by formula (VII),

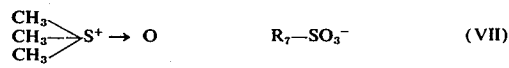

(VII)

wherein $R_7$ is the same as hereinbefore defined, per one mole of the penicillin sulfoxide at 95° to 120°C, preferably under reflux conditions for over one hour in one of the aforementioned inert organic solvents.

The scope of the penicillin sulfoxides used as the starting material in the process of the present invention, includes all penicillin sulfoxides except those which undergo undesirable side reactions under the reaction conditions used in the process of the present invention.

Suitable acyl groups $R_1$ of formulas I and III include for example, those acyl groups bonded to the 6-position of natural penicillin such as penicillin G, penicillin V, or the like, or synthetic penicillins such as α-phenoxypropylpenicillin (Propicillin), α-carboxybenzylpenicillin (Carbenicillin), 2,6-dimethoxyphenylpenicillin (Methicillin), 2-ethoxy-1-naphthylpenicillin, (Nafcillin), α-sulfonylbenzylpenicillin, α-azidobenzylpenicillin, 2-thienylpenicillin, α-aminobenzylpenicillin (Ampicillin) and the like, all of which may be protected. Suitable $R_2$ groups include those which can be easily removed in later steps, and are substantially nonreactive with the sulfonates represented by the formula (II). Moreover, they should be sufficiently stable to the reaction environment in the process of the invention. The $R_2$ groups include, for example, alkyl groups such as t-butyl, 2,2,2-trichloroethyl and the like and arylalkyl such as benzyl, p-ethoxybenzyl, p-nitrobenzyl, benzhydryl, trityl, phenacyl, and the like.

The sulfonates represented by formula (II) which are used in the process of the present invention are as follows.

Compounds of the formula (II), wherein A is

include the sulfonates of quaternary ammonium compounds derived from pyridine, substituted pyridine, quinoline, substituted quinoline, isoquinoline, substituted isoquinoline, dialkylanilines, trialkylamines, N-alkyl-piperidines, and the like such as, for example, N-methyl-pyridinium methanesulfonate, N-methylpyridinium p-toluenesulfonate, N-benzylpyridinium p-toluenesulfonate, N-methylpicolinium p-toluenesulfonate, N-methylquinolinium p-toluenesulfonate, N-benzylquinolinium chlorobenzenesulfonate, N-phenyl-N,N,N-trimethylammonium p-toluenesulfonate, N-phenyl-N,N-dimethyl-N-ethylammonium p-toluenesulfonate, N-benzyl-N,N,N-triethylammonium p-toluenesulfonate, N,N,N-triethyl-N-methylammonium p-toluenesulfonate, the inner salt of N-(3-sulfopropyl) pyridinium hydroxide and the like, and preferably N-methylpyridinium p-toluenesulfonate, N-methylpyridinium methanesulfonate, N-methylquinolinium p-toluenesulfonate, N,N,N-triethyl-N-methylammonium p-toluenesulfonate, and the like.

The compounds of formula (II), wherein A is

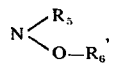

include those compounds derived from pyridine-N-oxide, substituted pyridine-N-oxide, quinoline-N-oxide, substituted quinoline-N-oxide, isoquinoline-N-oxide, dialkylaniline-N-oxide, N-alkylpiperidine-N-oxide, trialkylamine-N-oxide and the like, as, for example, N-methoxypyridinium, N-ethoxypyridinium, N-propoxypyridinium, N-benzyloxypyridinium, N-methoxypicolinium, N-methoxyquinolinium, N-methoxyisoquinolinium, N-methoxy-N,N-dimethyl-N-phenylammonium, N-methoxy-N,N,N-triethylammonium sulfonates and the like. The sulfonate anions include, for example, methanesulfonate, ethanesulfonate, propanesulfonate, benzenesulfonate, p-toluenesulfonate, 2,4,6-trimethylbenzenesulfonate, p-chlorobenzenesulfonate, naphthalenesulfonate and the like. Preferable sulfonate salts include N-methoxypyridinium methanesulfonate, N-methoxypyridinium p-toluenesulfonate, N-methoxyquinolinium p-toluenesulfonate and the like. Inner salts such as N-(3-sulfopropoxy)-pyridinium hydroxide, N-(3-sulfopropoxy)quinolinium hydroxide, and the like may also be used. N-(3-Sulfopropoxy)pyridinium hydroxide is particularly preferable.

The sulfonium sulfonates of formula (II) wherein A is S — $R_6$, include compounds derived from dialkyl sulfides, diarylalkyl sulfides, arylalkyl alkyl sulfides, alkyl aryl sulfides, tetrahydrothiophene, tetrahydrothiopyrane and the like such as, for example, S,S,S-trimethylsulfonium, S,S-diethyl-S-methylsulfonium, S,S-dipropyl-S-methylsulfonium, S,S-dibutyl-S-methyl-sulfonium, S,S,S-triethylsulfonium, S,S-dimethyl-S-benzylsulfonium, S,S-diethyl-S-benzylsulfonium, S,S-dipropyl-S-benzylsulfonium, S,S-dibutyl-S-benzylsulfonium, S,S-dimethyl-S-phenethylsulfonium, S-methyl-S,S-dibenzylsulfonium, S-ethyl-S,S-dibenzylsulfonium, S-methyl-S,S-bisphenethylsulfonium, S-ethyl-S,S-bisphenethylsulfonium, S-methyltetrahydrothiophenium, S-ethyltetrahydrothiophenium S-benzyltetrahydrothiophenium, S-phenethyltetrahydrothiophenium, S-methyltetrahydrothiopyranium, S-ethyltetrahydrothiopyranium sulfonate and the like. The sulfonate ions include, for example, methanesulfonate, ethanesulfonate, propanesulfonate, benzenesulfonate, p-toluenesulfonate, 2,4,6-trimethylbenzenesulfonate, dodecylbenzenesulfonate, p-chlorobenzenesulfonate, naphthalenesulfonate, and the like. Particularly preferable are S,S,S-trimethylsulfonium methanesulfonate, S,S-diethyl-S-methylsulfonium p-toluenesulfonate, S-methyltetrahydrothiophenium p-toluenesulfonate and the like. Inner salts such as S,S-diethyl(3-sulfopropyl)-sulfonium hydroxide, S,S-dibenzyl(3-sulfopropyl)sulfonium hydroxide, 3-sulfopropyltetrahydrothiophenium hydroxide and the like may also be used.

The sulfoxonium sulfonates of formula (II), wherein A is

include various $R_7$ sulfonates of S,S,S-trimethylsulfoxonium such as, for example, 1-12C alkanesulfonates such as methanesulfonate, ethanesulfonate, propanesulfonate, butanesulfonate, benzenesulfonate; alkylbenzenesulfonates such as p-toluenesulfonate, 2,4,6-trimethylbenzenesulfonate, dodecylbenzenesulfonate, and the like; naphthalenesulfonate, alkylnaphtahlenesulfonate, and the like. Particularly preferable are methanesulfonate, ethanesulfonate, propanesulfonate, butanesulfonate, benzenesulfonate, p-toluenesulfonate, dimethylbenzenesulfonate, trimethylbenzenesulfonate, 1-12C monoalkylbenzenesulfonate, and the like.

In the present invention, the sulfonates represented by the formula (II) are used in amounts of 0.1 to 4 moles, preferable 0.25 to 4 moles per mole of penicillin sulfoxide as the starting material. However, the amounts of the sulfonate used depends somewhat upon the type of compounds. It is most preferred that from 0.25 to 4 mole of a sulfonate represented by the formula (IV), from 0.25 to 1 mole of a sulfonate represented by the formula (V). from 0.5 to 4 mole of a sulfonate represented by the formula (VI) and from 0.5 to 4 mole of a sulfonate represented by the formula (VII) be used per one mole of the penicillin sulfoxide. The sulfonate compounds may be prepared in advance, or they may be produced in the reaction solution during use.

Suitable inert organic solvenst used in the process of the present invention include, for example 1,4-dioxane, n-propyl ether, methyl n-propyl ketone, methyl isobutyl ketone, ethyl carbonate, n-propyl acetate, 1,2-dichloropropane, 1,1,2-trichloroethane and the like.

Preferred solvents include 1,4-dioxane, methyl isobutyl ketone, 1,2-dichloropropane, 1,1,2-trichloroethane, and the like. When a sulfoxonium sulfonate is used as the sulfonate, 1,1,2-trichloroethane is preferably used.

The reaction of the process of the present invention is conducted at a temperature of over 50°C. However, because decomposition products are gradually increasingly produced at temperatures over 160°C, it is desirable to maintain the temperature below 160°C. Accordingly, it is most advantageous to conduct the reaction at 80° to 130°C, preferably 90° to 115°C. However, when a sulfoxonium sulfonate is used, the reaction is preferably conducted at 95° to 120°C, and particularly at the reflux temperature of the medium.

Since the reaction time is affected by the reaction temperature, the type and amount of sulfonate and the type of inert solvent, it is not always constant. However, the reaction time is at least 30 minutes. Generally, the reaction is almost finished in 30 minutes to 24 hours.

Certain amounts of water are produced as the reaction proceeds in the process of the present invention. However, these quantities of water may desirably be easily removed by conventional methods such as passing the solution through a dehydrating agent when the evaporated solvent to be returned to the reaction container is condensed in a condenser.

It is not necessary to adopt a particular method of separating and purifying the desacetoxy cephalosporanic acid compounds produced from the reaction mixture, but the conventional means often used for these purposes may be effectively used. For example, the desired product may be easily obtained by extraction and cleaning techniques with crystallization using a solvent such as water, 1,4-dioxane, diethyl ether, dichloromethane, chloroform, ethyl acetate, benzene, acetone, methanol, ethanol, isopropanol, or the like.

Some of the compounds represented by formula (V) and (VII) used in the process of the present invention are previously unknown compounds, and these compounds may be easily synthesized by the following method: The sulfonate represented by the formula(V) may be easily synthesized by heating the compound of formula (VIII),

(VIII)

wherein $R_3$, $R_4$ and $R_5$ are the same as hereinbefore defined, and a sulfonate represented by the formula (IX),

(IX)

wherein $R_6$ and $R_7$ are the same as hereinbefore defined.

Sulfonates represented by the formula (VI) are easily prepared by allowing IX and X to stand at room temperature or by heating a sulfide represented by the formula (X) with sulfonate (IX)

(X)

wherein $R_3$ and $R_4$ are the same as hereinbefore defined. Sulfonates of formula VI can also be prepared by treating the sulfonium iodide obtained by reacting a compound represented by the formula (X) with an alkyl iodide, with silver oxide to form a sulfonium hydroxide. The hydroxide is then reacted with a sulfonic acid.

Sulfoxonium sulfonates represented by the formula (VII) are prepared by a method in which dimethylsulfoxide is reacted with a methyl halide to form a S,S,S-trimethylsulfoxonium halide and then treating the S,S,S-trimethylsulfoxonium halide thus obtained with silver oxide to form S,S,S-trimethylsulfoxonium hydroxide. The hydroxide is then reacted with a sulfonic aicd. Alternatively, dimethyl sulfoxide is heated with the methyl ester or a sulfonic acid.

Having generally described this invention, a further understanding can be obtained by reference to certain specific examples which are provided herein for purposes of illustration only, and are not intended to be limiting unless otherwise specified.

EXAMPLE 1

A 220.3 mg (2 millimole) quantity of methyl methanesulfonate and 158.2 mg (2millimole) of dry pyridine were dissolved in 80 ml of dry dioxane, and were heated under reflux for one hour to produce N-methylpyridinium methanesulfonate. To the salt was added 914 mg (2 millimole) or the p-methoxybenzyl ester of benzylpenicillin sulfoxide and the mixture was heated under reflux for 11 hours. At this time, a condensed solvent was passed through calcium oxide before the condensed solvent was returned to the reaction container or vessel. After the completion of the reaction, the insoluble materials were removed therefrom, and the solvent was evaporated under reduced pressure. The residue was dissolved in 50 ml of ethyl acetate, and after the solution was washed with water and dried, ethyl acetate was distilled. When the product thus obtained was washed with diethyl ether, 604.7 mg (66.9%) of the p-methoxybenzyl ester of 7-phenylacetamidodesacetoxy cephalosporanic acid having a melting point of 162.5° to 168°C were obtained. The acid was very pure. However, recrystallization of the acid gave a completely pure product having a melting point of 179.5° to 181°C.

The cephalosporanic acid had the following optical and spectral properties:
$[\alpha]_D^{20} + 36.7°$ (C = 1.5, CHCl$_3$)
UV $\lambda$max. (MeOH): 226 m$\mu$ ($E_{1cm}^{1\%}$ 486)
264 – 270 m$\mu$ ($E_{1cm}^{1\%}$ 227)
IR $\nu_{max}^{kBr}$: 3245 cm$^{-1}$ (NH), 1760 cm$^{-1}$ ($\beta$-lactam)
1715 cm$^{-1}$ (CO$_2$R), 1655 cm$^{-1}$ (CONH)
NMR $\tau$ (CDCl$_3$, 60MHz)

| | | | |
|---|---|---|---|
| 7.94(3H, s, 3-CH$_3$ | )6.77(2H, | AB-q, S—CH$_2$— | ) |
| 6.43(2H, s, Ph-CH$_2$— | )6.26(3H, | s, OCH$_3$ | ) |
| 5.17(1H, d, 8 - H | )4.88(2H, | s, OCH$_2$— | ) |
| 4.33(1H, q, 7 - H | )3.35(1H, | d, NH | ) |
| 2.97(4H, q, —C$_6$H$_4$— | )2.77(5H, | s, C$_6$H$_5$— | ) |

It was established by means of thin layer chromatographs, IR and NMR analysis that the wash solutions of diethyl ether contained considerable amounts of the p-methoxybenzylester of 7-phenylacetamidodesacetoxy cephalosporanic acid.

EXAMPLE 2

The procedure of Example 1 was repeated under the same reaction conditions except that 1.489 g (8 millimole) of methyl p-toluenesulfonate, 632.8 mg (8 millimole) of dry pyridine and 941 mg (2millimole) of the p-methoxybenzyl ester of benzylpenicillin sulfoxide were reacted for 7.5 hours. By this procedure 612.1 mg (67.7%) of considerably pure p-methoxybenzylester of 7-phenylacetamidodesacetoxy cephalosporanic acid having a melting point of 153.5° to 160°C were obtained. When this product was recrystallized, it was further purified and had a melting point of 179.5° to 181°C. The wash solutions of diethyl ether contained considerable amounts of the p-methoxybenzylester of 7-phenylacetamidodesacetoxy cephalosporanic acid.

EXAMPLE 3

The procedure of Example 1 was repeated under the same reaction conditions except that 93.1 mg (0.5 millimole) of methyl p-toluenesulfonate, 35.9 mg (0.5 millimole) of dry pyridine, and 941 mg (2 millimole) of the p-methoxybenzylester of benzylpenicillin sulfoxide were reacted for 14.5 hours. By this procedure 498 mg (55.1%) of considerably pure p-methoxybenzyl ester of 7-phenylacetamidodesacetoxy cephalosporanic acid having a melting point of 154° to 161°C were obtained. When this product was recrystallized, it was further purified and had a melting point of 179.5° to 181°C.

EXAMPLE 4

The procedure of Example 1 was repeated under the same reaction conditions except that 372.5 mg (2 millimole) of methyl p-toluenesulfonate, 258.3 mg (2 millimole) of dry quinoline and 941 mg (2 millimole) of the p-methoxybenzyl ester of benzylpenicillin sulfoxide were reacted for 8 hours. By this procedure 570.8 mg (63.1%) of considerable pure p-methoxybenzylester of 7-phenylacetamidodesacetoxy cephalosporanic acid having a melting point of 156° to 163°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 5

The procedure of Example 1 was repeated under the same reaction conditions except that 372.5 mg (2 millimole) of methyl p-toluenesulfonate, 242.4 mg (2 millimole) of N,N-dimethylaniline, and 941 mg (2 millimole) of the p-methoxy-benzylester of benzylpenicillin sulfoxide were reacted for 9.5 hours. By this procedure 561.5 mg (62.1%) of the p-methoxy-benzylester of 7-phenylacetamidodesacetoxy cephalosporanic acid having a melting point of 140° to 153° C were obtained. When this product was recrystallized, it was further purified and had a melting point of 179.5° to 181° C. The wash solutions of diethyl ether contained considerable amounts of the p-methoxybenzylester of 7-phenylacetamidodesacetoxy cephalosporanic acid.

EXAMPLE 6

The procedure of Example 1 was repeated under the same reaction conditions except that 524.2 mg (2 millimole) of benzyl p-toluenesulfonate, 158.2 mg (2 millimole) of dry pyridine, and 941 mg (2 millimole) of the p-methoxybenzylester of benzylpenicillin sulfoxide were obtained. By this procedure 517.7 mg (57.3%) of the p-methoxybenzyl ester of 7-phenylacetamidodesacetoxy cephalosporanic acid having a melting point of 145.5° to 158.5°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 7

Preparation of N-methoxypyridinium methanesulfonate

N-methoxypyridinium methanesulfonate was prepared by mixing pyridine N-oxide and an equimolar amount of methylmethanesulfonate and heating the mixture at 95°C for 6 hours. The crude product obtained was recrystallized in a mixture of ethanol and ethyl acetate. By this procedure N-methoxypyridinium methanesulfonate having a melting point of 83° to 85.5°C were obtained.

Preparation of 7-phenylacetamidodesacetoxy cephalosporanic acid

A 941 mg (2 millimole) quantity of the p-methoxybenzyl ester of benzylpenicillin sulfoxide and 410.5 mg (2 millimole) of N-methoxypyridinium methanesulfonate were heated under reflux conditions for 7 hours in 80 ml of dry dioxane. The dioxane was dried by passing the condensed solvent through calcium oxide before the condensed solvent was returned to the reaction vessel. After the reaction was completed, insoluble material was removed therefrom and the solvent was distilled under reduced pressure. The residue was dissolved in 50 ml of ethyl acetate, and after the solution was washed with water and dried, ethyl acetate was distilled. When the product thus obtained was washed with diethyl ether, 512.8 mg (56.7%) of considerably pure p-methoxybenzylester of 7-phenylacetamidodesacetoxy cephalosporanic acid having a melting point of 157.5° to 165°C were obtained. After recrystallization of the product, it was further purified and had a melting point of 179.5° to 181°C.

The cephalosporanic acid had the following optical and spectral properties:

$[\alpha]_D^{20} + 36.7°$ (C = 1.5, CHCl$_3$)
UV$\lambda$max (MeOH): 226 m$\mu$ (E$_{1cm}^{1\%}$ 486)
264 – 270 m$\mu$ (E$_{1cm}^{1\%}$ 227)
IR$\nu_{max}^{KBr}$: 3245 cm$^{-1}$ (NH), 1760 cm$^{-1}$ ($\beta$-lactam)
1715 cm$^{-1}$ (CO$_2$R), 1655 cm$^{-1}$ (CONH)
NMR$\tau$(CDCl$_3$, 60MHz)

| | | |
|---|---|---|
| 7.94(3H, s, 3-CH$_3$ | )6.77(2H, | AB-q, s-CH$_2$— ) |
| 6.43(2H, s, Ph-CH$_2$— | )6.26(3H, | s, OCH$_3$ ) |
| 5.17(1H, d, 8 - H | )4.88(2H, | s, OCH$_2$— ) |
| 4.33(1H, q, 7 - H | )3.35(1H, | d, NH ) |
| 2.97(4H, q, —C$_6$H$_4$— | )2.77(5H, | s, C$_6$H$_5$— ) |

The wash solutions of diethyl ether as established by means of thin layer chromatography, IR and NMR analysis contained considerable amounts of p-methoxybenzylester of 7-phenylacetamidedesacetoxy cephalosporanic acid.

EXAMPLE 8

Preparation of 7-phenylacetamidodesacetoxy cephalosporanic acid

The procedure of Example 7 was repeated under the same reaction conditions except that 941 mg (2 millimole) of the p-methoxybenzylester of benzylpenicillin sulfoxide and 281.3 mg (1 millimole) of N-methoxypyridinium p-toluenesulfonate were reacted for 5 hours. By this procedure 490.0 mg (54.2%) of the p-methoxybenzylester of 7-phenylacetamidodesacetoxy cephalosporanic acid having a melting point of 149.5° to 157.5°C were obtained. The isolated product was conderably pure. However, recrystallization of the product gave a completely pure product having a melting point of 179.5° to 181°C. The wash solutions of diethyl ether contained considerable amounts of p-methoxybenzyl ester of 7-phenylacetamidodesacetoxy cephalosporanic acid.

EXAMPLE 9

Preparation of N-Benzyloxypyridinium p-toluenesulfonate

N-Benzyloxypyridinium p-toluenesulfonate was prepared by mixing pyridine-N-oxide and an equimolar amount of benzyl p-toluenesulfonate and heating the mixture at 85°C for 4 hours. The crude product was recrystallized from a mixture of ethanol and ethyl acetate. By this procedure N-benzyloxypyridinium p-toluenesulfonate having a melting point of 107° to 109°C was obtained.

Preparation of 7-phenylacetamidodesacetoxy cephalosporanic acid

The procedure of Example 7 was repeated under the same reaction conditions except that 941 mg (2 millimole) of the p-methoxybenzyl ester of benzylpenicillin sulfoxide and 178.6 mg (0.5 millimole) of N-benzyloxypyridinium p-toluenesulfonate were reacted for 7 hours. By this procedure 535.3 mg (59.2%) of the p-methoxybenzyl ester of 7-phenylacetamidodesacetoxy cephalosporanic acid having a melting point of 140° to 161°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 10

Preparation of N-methoxyquinolinium p-toluenesulfonate

N-Methoxyquinolinium p-toluenesulfonate was prepared by mixing quinoline-N-oxide and an equimolar amount of methyl p-toluenesulfonate and heating the mixture at 95°C for 5 hours. The crude product was recrystallized from a mixture of methanol and ethyl acetate. By this procedure N-methoxyquinolinium p-toluenesulfonate was obtained. The salt had the following features in the NMR:

NMR (CDCl$_3$, 60MHz)
7.77(3H, s,)
5.45(3H, s,)
2.60(4H, q,)
−0.3 to 2.1(7H, m,)

Preparation of 7-phenylacetamidodesacetoxy cephalosporanic acid

The procedure of Example 7 was repeated under the same reaction conditions except that 941 mg (2 millimole) of the p-methoxybenzyl ester of benzylpenicillin sulfoxide and 331.0 mg (1 millimole) of N-methoxyquinolinium p-toluenesulfonate were reacted for 5 hours. By this procedure 629.6 mg (69.6%) of the p-methoxybenzyl ester of 7-phenylacetamidodesacetoxy cephalosporanic acid having a melting point of 148° to 154.5°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 11

The procedure of Example 7 was repeated under the same reaction conditions except that 941 mg (2 millimole) of the p-methoxybenzyl ester of benzylpenicillin sulfoxide and 434.3 mg (2 millimole) of the inner salt of N-(3-sulfopropoxy)pyridinium hydroxide were reacted for 35 hours. By this procedure the p-methoxybenzyl ester of 7-phenylacetamidodesacetoxy cephalosporanic acid was obtained. When this product was recrystallized, it was further purified and had a melting point of 179.5° to 181°C.

EXAMPLE 12

Preparation of S,S-diethyl S-methylsulfonium p-toluenesulfonate

White crystals of diethylmethylsulfonium p-toluenesulfonate (10.04g) having a melting point of 56° to 58°C were obtained by allowing a mixture of 4.51g of diethylsulfide and 931 g of methyl p-toluenesulfonate to stand for three days at room temperature. The crystals were collected by filtration and were washed with diethyl ether and dried. After the toluenesulfonate was recrystallized, it had a melting point of 56.5° to 59°C.

Preparation of 7-phenylacetamidodesacetoxy cephalosporanic acid

A 941 mg (2 millimole) quantity of the p-methoxybenzyl ester of benzylpenicillin sulfoxide and 276.4 mg (1 millimole) of S,S-diethyl S-methylsulfonium p-toluenesulfonate were heated under reflux conditions in 80 ml of dry dioxane for 9 hours. The dioxane was dried by passing the condensed solvent through calcium oxide before the condensed solvent was returned to the reaction vessel. After completion of the reaction, insoluble material was removed therefrom, the solvent was distilled under reduced pressure, the residue was dissolved in 50 ml of ethyl acetate, and after the solution was washed with water and dried, ethyl acetate was distilled. After the product thus obtained was washed with diethyl ether, 548.4 mg (60.7%) of the p-methoxybenzyl ester of 7-phenylacetamidodesacetoxy cephalosporanic acid having a melting point of 161° to 165°C were obtained. The acid obtained was considerably pure. However, upon further recrystallization, it was completely purified and had a melting point of 179.5° to 181°C.

The cephalosporanic acid had the following optical and spectral properties:
$[\alpha]_D^{20} + 36.7°$ (C = 1.5, CHCl$_3$)
UVλmax (MeOH): 226 mμ ($E_{1cm}^{1\%}$ 486)
264 − 270 mμ ($E_{1cm}^{1\%}$ 227)
IR$\nu_{max}^{KBr}$: 3245 cm$^{-1}$ (NH), 1760 cm$^{-1}$ (β-lactam)
1715 cm$^{-1}$ (CO$_2$R), 1655 cm$^{-1}$ (CONH)
NMRτ(CDCl$_3$, 60MHz)

| | | | |
|---|---|---|---|
| 7.94(3H, s, 3-CH$_3$ | )6.77(2H, | AB-q, S—CH$_2$— | ) |
| 7.43(2H, s, ph-CH$_2$— | )6.26(3H, | s, OCH$_3$ | ) |
| 5.17(1H, d, 8 - H | )4.88(2H, | s, O—CH$_2$— | ) |
| 4.33(1H, q, 7 - H | )3.35(1H, | d, NH | ) |
| 2.97(4H, q, —C$_6$H$_4$— | )2.77(5H, | s, C$_6$H$_5$— | ) |

The wash solutions of diethyl ether contained considerable amounts of the p-methoxybenzyl ester of 7-phenylacetamidodesacetoxy cephalosporanic acid as established by means of thin layer chromatography, IR and NMR analysis.

EXAMPLE 13

The procedure of Example 12 was repeated under the same reaction conditions except that 941 mg (2 millimole) of the p-methoxybenzyl ester of benzylpenicillin sulfoxide and 2211.2 mg (8 millimole) of S,S-diethyl S-methylsulfonium p-toluenesulfonate were reacted for 4 hours. By this procedure 544 mg (60.2%) of the p-methoxybenzyl ester of 7-phenylacetamidodesacetoxy cephalosporanic acid having a melting point of 156° to 162.5°C were obtained. The acid product obtained was considerably pure. However, recrystallization of the acid gave a completely pure product having a melting point of 179.5° to 181°C. The wash solutions of diethyl ether contained considerable amounts of the p-methoxybenzyl ester of 7-phenylacetamidodesacetoxy cephalosporanic acid.

EXAMPLE 14

The procedure of Example 12 was repeated under the same reaction conditions except that 941 mg (2 millimole) of the p-methoxybenzyl ester of benzylpenicillin sulfoxide and the inner salt of S,S-dibenzyl-(3-sulfopropyl)sulfonium hydroxide inner salt were reacted for 5 hours. By this procedure 726.6 mg (80.4%) of the p-methoxybenzyl ester of 7-phenylacetamidodesacetoxy cephalosporanic acid having a melting point of 138.5° to 146.5°C were obtained. When this product was recrystallized, it was further purified and had a melting point of 179.5° to 181°C. The wash solutions of diethyl ether contained considerably amounts of the p-methoxybenzyl ester of 7-phenylacetamidodesacetoxy cephalosporanic acid.

EXAMPLE 15

The procedure of Example 12 was repeated under the same reaction conditions except that 941 mg (2 millimole) of the p-methoxybenzyl ester of benzylpenicillin sulfoxide and 648.5 mg (2 millimole) of S-benzyl S,S-dimethylsulfonium p-toluenesulfonate were reacted for 8 hours. By this procedure 630.2 mg (69.7%) of the p-methoxybenzyl ester of 7-phenylacetamidodesacetoxy cephalosporanic acid having a melting point of 130.5° to 140°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 16

Preparation of S,S-dibenzyl S-methylsulfonium p-toluenesulfonate

A 2.03 g yield of crystals of S,S-dibenzyl S-methylsulfonium p-toluenesulfonate having a melting point of 136° to 137°C was obtained by allowing a mixture of 5.36 g of dibenzylsulfide and 4.66 g of methyl p-toluenesulfonate to stand for 2 weeks at room temperature in dry benzene. The crystals were collected by filtration and were washed with benzene and then dried. When this was recrystallized, it showed a melting point of 137° to 137.5°C.

Preparation of 7-phenylacetamidodesacetoxy cephalosporanic acid

The procedure of Example 12 was repeated under the same reaction conditions except that 941 mg (2 millimole) of the p-methoxybenzyl ester of benzylpenicillin sulfoxide and 801.1 mg (2 millimole) of S,S-dibenzyl S-methylsulfonium p-toluenesulfonate were reacted for 20 hours. By this procedure 641.3 mg (70.9%) of the p-methoxybenzyl ester of p-phenylacetamidodesacetoxy cephalosporanic acid having a melting point of 120° to 130°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 17

Preparation of S,S,S-trimethylsulfonium methane sulfonate

A mixture of 1.24 g of dimethylsulfide and 2.20 g of methyl methanesulfonate was allowed to stand for three days at room temperature. The crystals which deposited were collected by filtration, washed with diethyl ether and dried. By this procedure crystals of S,S,S-trimethylsulfonium methanesulfonate were obtained. When this product was recrystallized, it had a melting point of 193.0° to 195.0°C.

Preparation of 7-phenylacetamidodesacetoxy cephalosporanic acid

A 941 mg (2 millimole) quantity of the p-methoxybenzyl ester of benzylpencillin sulfoxide and 344.5 mg (2 millimole) of S,S,S-trimethylsulfonium methanesulfonate were heated mildly under the reflux conditions for 4 hours in 80 ml of 1,1,2-trichloroethane. After completion of the reaction, the procedure of Example 12 was repeated under the same reaction conditions. By this procedure 556.8 mg (61.6%) of the p-methoxybenzyl ester of 7-phenylacetamidodesacetoxy cephalosporanic acid having a melting point of 157° to 163° C were obtained. The product obtained was considerably pure. However, after it was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 18

Preparation of S-methyltetrahydrothiophenium p-toluenesulfonate

A mixture of 1.76 g of tetrahydrothiophene and 3.72 g of methyl p-toluenesulfonate was allowed to stand for 3 days at room temperature. The crystals which were deposited were collected by filtration, washed with diethyl ether, and dried. By this procedure crystals of S-methyltetrahydrothiophenium p-toluenesulfonate were obtained. After the product was recrystallized, it had a melting point of 145.0° to 148.0°C.

Preparation of 7-phenylacetamidodesacetoxy cephalosporanic acid

The procedure of Example 12 was repeated under the same reaction conditions except that 941 mg (2 millimole of the p-methoxybenzyl ester of benzylpenicillin sulfoxide and 548.8 mg (2 millimole) of S-methyltetrahydrothiophenium p-toluenesulfonate were reacted for 9 hours. By this procedure 565.2 mg (62.6%) of the p-methoxybenzyl ester of 7-phenylacetamidodesacetoxy cephalosporanic acid having a melting point of 145° to 155°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 19

Preparation of S,S,S-trimethylsulfoxonium ethane sulfonate

A 3.0 g amount of S,S,S-trimethylsulfoxonium iodide was dissolved in 300 ml of water and 6.0 g of silver oxide was added thereto. The system was flushed with nitrogen gas, shielded from light, and then was shaken for 20 minutes. The precipitate which formed was quickly filtered and an aqueous solution of 10% ethanesulfonic acid was immediately added to the filtrate with stirring and the pH thereof was adjusted to 3.2. After the solution was decolorized with active carbon, crystals of crude product were obtained by distilling the water solvent under reduced pressure. The product was recrystallized from alcohol, and S,S,S-trimethylsulfoxonium ethanesulfonate (63.8%) having a melting point of 207.0° to 207.5°C was obtained.

Elemental analysis: $C_5H_{14}O_4S_2$: Calculated: C: 29.69%, H: 6.98%; Found: C: 29.73%, H: 7.13%

Preparation of 7-phenylacetamidodesacetoxy cephalosporanic acid

A 941 mg (2 millimole) amount of the p-methoxybenzyl ester of benzylpenicillin sulfoxide and 405 mg (2 millimole) of S,S,S-trimethylsulfoxonium ethane sulfonate were mildly heated under reflux conditions for 17 hours in 80 ml of 1,1,2-trichloroethane. After completion of the reaction, insoluble material was removed therefrom. The solvent was distilled under reduced pressure and the residue was dissolved in 50 ml of ethyl acetate. The acetate solution was washed with water and dried, and then ethyl acetate was distilled. The product thus obtained was washed with diethyl ether. By this procedure 348.0 mg (3.5%) of the p-methoxybenzyl ester of 7-phenylacetamidodesacetoxy cephalosporanic acid having a melting point of 165° to 169°C were obtained. The product obtained was considerably pure. Upon recrystallization, it was further purified and had a melting point of 179.5° to 181°C.

The cephalosporanic acid had the following optical and spectral properties:

$[\alpha]_D^{20} + 36.7°$ (C = 1.5, CHCl$_3$)
UV λmax (MeOH): 226 mμ ($E_{1cm}^{1\%}$ 486) 264 – 270 mμ ($E_{1cm}^{1\%}$ 227)
IR $\nu_{max}^{KBr}$: 3245 cm$^{-1}$ (NH), 1760 cm$^{-1}$ (β-lactam) 1715 cm$^{-1}$ (CO$_2$R), 1655 cm$^{-1}$ (CONH)
NMR τ(CDCl$_3$, 60MHZ)

| | | |
|---|---|---|
| 7.94(3H, s, 3-CH$_3$ | )6.77(2H, | AB-q, S—CH$_2$— ) |
| 6.43(2H, s, Ph-CH$_2$— | )6.26(3H, | s, OCH$_3$ ) |
| 5.17(1H, d, 8 - H | )4.88(2H, | s, OCH$_2$— ) |
| 4.33(1H, q, 7 - H | )3.35(1H, | d, NH ) |
| 2.97(4H, q, —C$_6$H$_4$— | )2.77(5H, | s, C$_6$H$_5$— ) |

The wash solutions of diethyl ether contained considerable amounts of the p-methoxybenzyl ester of 7-phenylacetamidodesacetoxy cephalosporanic acid as established by means of this layer chromatography, IR and NMR.

EXAMPLE 20

Preparation of S,S,S-trimethylsulfoxonium methanesulfonate

A 50 g amount of dimethylsulfoxide and 10 g of methyl methanesulfonate were heated and stirred under reflux conditions at 100°C for 20 hours. The mixture was allowed to stand at room temperature and crystals of a product were collected by filtration. The crystals were then washed with acetone yielding 5.97 g of a white, crystalline product. When this product was recrystallized from alcohol, S,S,S-trimethylsulfoxonium methanesulfonate having a melting point of 222.0° to 222.5°C. (decomposition) was obtained.

Elemental analysis: $C_4H_{12}O_4S_2$: Calculated C: 25.52%, H: 6.43%; Found: C: 25.55%, H: 6.53%.

Preparation of 7-phenylacetamidodesacetoxy cephalosporanic acid

The procedure of Example 19 was repeated under the same reaction conditions except that 941 mg (2 millimole) of the p-methoxybenzyl ester of benzylpenicillin sulfoxide and 376.5 mg (2 millimole) of S,S,S-trimethylsulfoxonium methane sulfonate were reacted for 35 hours. By this procedure 373.7 mg (41.3%) of the p-methoxybenzyl ester of 7-phenylacetamidodesacetoxy cephalosporanic acid having a melting point of 153° to 157.5°C were obtained. The product obtained had considerable purity. Upon recrystallization, however, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 21

The procedure of Example 19 was repeated under the same reaction conditions except that 941 mg (2 millimole) of the p-methoxybenzyl ester of benzylpenicillin sulfoxide and 528.7 mg (2 millimole) of S,S,S-trimethylsulfoxonium p-toluenesulfonate were reacted for 8 hours. By this procedure 319.1 mg (35.3%) of the p-methoxybenzyl ester of 7-phenylacetamidodesacetoxy cephalosporanic acid having a melting point of 159° to 166.5°C were obtained. The product obtained had considerable purity. However, upon recrystallization it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 22

Preparation of S,S,S,-trimethylsulfoxonium benzenesulfonate

A 3.0 g amount of S,S,S-trimethylsulfoxonium iodide was dissolved in 300 ml of water and 6.0 g of silver oxide was added thereto. The reaction system was flushed with nitrogen gas, shielded from light, and shaken for 20 minutes. The precipitated product was quickly filtered. An aqueous 10% benzenesulfonic acid solution was immediately added to the filtrate with stirring, and the pH thereof was adjusted to 3.2. The acid solution was decolorized with activated carbon. The crystals obtained by distilling the water solvent under reduced pressure were recrystallized in a mixture of methanol and ethanol. By this procedure S,S,S-trimethylsulfoxoniumbenzene sulfonate (66.6%) having a melting point of 171.5° to 173°C was obtained.

Elemental analysis: $C_9H_{14}O_4S_2$: Calculated: C: 43.18%, H: 5.64%; Found: C: 43.17%, H: 5.62%

Preparation of 7-phenylacetamidodesacetoxy cephalosporanic acid

The procedure of Example 19 was repeated under the same reaction conditions except that 941 mg (2 millimole) of the p-methoxybenzyl ester of benzylpenicillin sulfoxide and 500 mg (2 millimole) of S,S,S-trimethylsulfoxonium benzene sulfonate were reacted for 13 hours. By this procedure 332.6 mg (36.8%) of the p-methoxybenzyl ester of 7- phenylacetamidodesacetoxy cephalosporanic acid having a melting point of 159° to 163°C were obtained. The product had considerable purity. However, upon recrystallization, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 23

Preparation of S,S,S-trimethylsulfoxonium-2,4,6-trimethylbenzenesulfonate

A 3.0 g amount of S,S,S-trimethylsulfoxonium iodide was dissolved in 300 ml of water and 6.0 g of silver oxide was added thereto. The reaction system was flushed with nitrogen gas, shielded from light, and shaken for 20 minutes. The product which precipitated was immediately filtered, and an aqueous 10% 2,4,6-trimethylbenzenesulfonic acid solution was added immediately to the filtrate while stirring to adjust the pH to 3.2. The filtrate was decolorized with activated carbon and the solvent was removed by distillation under reduced pressure. The white crystals thus obtained were recrystallized from alcohol, and 2.80 g (70.3%) of S,S,S-trimethylsulfoxonium-2,4,6-trimethylbenzenesulfonate having a melting point of 189° to 191°C (decomposition) was obtained.

Elemental analysis: $C_{12}H_{20}O_4S_2$: Calculated: C: 49.29%, H: 6.89%; Found: C: 49.08%, H: 6.98%

Preparation of 7-phenylacetamidodesacetoxy cephalosporanic acid

The procedure of Example 19 was repeated under the same reaction conditions except that 941 mg (2 millimole) of the p-methoxybenzyl ester of benzylpenicillin sulfoxide and 586 mg (2 millimole) of S,S,S-trimethylsulfoxonium-2,4,6-trimethylbenzene sulfonate were reacted for 13 hours. By this procedure 462.1 mg (51.1%) of the p-methoxybenzyl ester of 7-phenylacetamidodesacetoxy cephalosporanic acid having a melting point of 146.5°to 155.6°C were obtained. When this product was recrystallized, it was further purified and had a melting point of 179.5° to 181°C. The wash solutions of diethyl ether contained the p-methoxybenzyl ester of 7-phenylacetamidodesacetoxy cephalosporanic acid.

EXAMPLE 24

Preparation of S,S,S-trimethylsulfoxonium-β-naphtahlene sulfonate

A 3.0 g amount of S,S,S-trimethylsulfoxonium iodide was dissolved in 300 ml of water and 6.0 g of silver oxide were added thereto. The reaction system was flushed with nitrogen gas, shielded from light, and shaken for 20 hours. The product which precipitated was immediately filtered, and an aqueous 10%-β-naphthalenesulfonic acid solution was immediately added to the filtrate with stirring. The pH was adjusted to 3.2. After the solution was decolorized with activated carbon, the solvent was removed by distillation under reduced pressure. The crystals thus obtained were recrystallized from alcohol, and S,S,S-trimethylsulfoxonium-β-naphthalene sulfonate (63.2%) having a melting point of 206.0° to 207.0°C was obtained.

Elemental analysis: $C_{13}H_{16}O_4S_2$: Calculated: C: 51.98%, H: 5.37%; Found: C: 51.92%, H: 5.40%

Preparation of 7-phenylacetamidodesacetoxy cephalosporanic acid

The procedure of Example 19 was repeated under the same reaction conditions except that 941 mg (2 millimole) of the p-methoxybenzyl ester of benzylpenicillin sulfoxide and 536 mg (1.78 millimole) of S,S,S-trimethylsulfoxonium-β-naphthalene sulfonate were reacted for 11.5 hours. By this procedure 295.5 mg (32.7%) of the p-methoxybenzyl ester of 7-phenylacetamidodesacetoxy cephalosporanic acid having a melting point of 153.5° to 161.6°C were obtained. The product obtained was of considerable purity. However, upon recrystallization, it was further purified and had a melting point of 179.5° to 181°C. The wash solution of diethyl ether contained considerable amounts of the p-methoxybenzyl ester of 7-phenylacetamidodesacetoxy cephalosporanic acid.

EXAMPLE 25

Preparation of S,S,S-trimethylsulfoxonium dodecylbenzene sulfonate

A 3.0 g amount of S,S,S-trimethylsulfoxonium iodide was dissolved in 300 ml of water and 6.0 g of silver oxide were added thereto. The reaction system was flushed with nitrogen gas, shielded from light, and shaken for 20 minutes. The product which precipitated was quickly filtered and an aqueous 10% dodecylbenzene sulfonic acid solution was immediately added to the filtrate to adjust the pH to 3.2. The acid solution was then decolorized with activated carbon and the solvent was removed by distillation under reduced pressure. The crystals thus obtained were recrystallized in a mixture of ethanol and ethyl acetate. By this procedure, crystals of S,S,S-trimethylsulfoxoniumdodecylbenzene sulfonate having a melting point of 181.0° to 190.5°C were obtained.

Elemental analysis: $C_{21}H_{38}O_4S_2$: Calculated: C: 60.25%, H: 9.15%; Found: C: 60.19%, H: 8.97%

Preparation of 7-phenylacetamidodesacetoxy cephalosporanic acid

The procedure of Example 19 was repeated under the same reaction conditions except that 941 mg (2 millimole) of the p-methoxybenzyl ester of benzylpenicillin sulfoxide and 837.3 mg (2 millimole) of S,S,S-trimethylsulfoxoniumdodecylbenzenesulfonate were reacted for 4.5 hours. By this procedure 331.5 mg (36.7%) of the p-methoxybenzyl ester of 7-phenylacetamidodesacetoxy cephalosporanic acid having a melting point of 161.5° to 167.0°C were obtained. The product obtained had considerable purity. However, upon recrystallization, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 26

A 941 mg amount (2 millimole) of the p-methoxybenzyl ester of benzylpenicillin sulfoxide and 418.7 mg (1 millimole) of S,S,S-trimethylsulfoxoniumdodecylbenzene sulfonate were heated under reflux conditions for 11.5 hours in 80 ml of dry dioxane. The dried dioxane solvent was obtained by passing the condensed solvent through calcium oxide before the condensed solvent was returned to the reaction vessel. After completion of the reaction, the procedure of Example 19 was repeated under the same reaction conditions. By this procedure 463.1 mg (51.2%) of the p-methoxybenzyl ester of 7-phenylacetamidodesacetoxy cephalosporanic acid having a melting point of 143.5° to 155.0°C were obtained. When this product was recrystallized, it was further purified and had a melting point of 179.5° to 181°C. The wash solutions of diethyl ether contained considerable amounts of the p-methoxybenzyl ester of 7-phenylacetamidodesacetoxy cephalosporanic acid.

EXAMPLE 27

A 941 mg (2 millimole) amount of the p-methoxybenzyl ester of benzylpenicillin sulfoxide and 574.8 mg of N,N,N-triethyl-N-methylammonium p-toluenesulfonate were heated under reflux conditions for 5.5 hours in 80 ml of dry dioxane. The dried dioxane solvent was prepared by passing the condensed solvent through calcium oxide before the condensed solvent was returned to the reaction vessel. Thereafter, the procedure of Example 1 was repeated under the same reaction conditions. By this procedure 536.0 mg (59.3%) of considerably pure 7-phenylacetamidodesacetoxy cephalosporanic acid having a melting point of 158.5° to 165.0°C were obtained. When this product was recrystallized, it was further purified and had a melting point of 179.5° to 181°C. The wash solutions of diethyl ether contained the p-methoxybenzyl ester of 7-phenylacetamidodesacetoxy cephalosporanic acid.

EXAMPLE 28

Preparation of 7-phenylacetamidodesacetoxy cephalosporanic acid

A 941 mg (2 millimole) amount of the p-methoxybenzyl ester of benzylpenicillin sulfoxide and 434.4 mg (2 millimole) of the inner salt of N-(3-sulfopropoxy)-pyridinium hydroxide were mildly heated under reflux conditions for 9 hours in 80 ml of 1,1,2-trichloroethane. After completion of the reaction, the procedure of Example 7 was repeated under the same reaction conditions. By this procedure 498.6 mg (55.2%) of the p-methoxybenzyl ester of 7-phenylacetamidodesacetoxy cephalosporanic acid having a melting point of 156° to 161.5°C were obtained. The product obtained had considerable purity. However, upon recrystallization, it was further purified and had a melting point of 179.5° to 181°C. The wash solutions of diethyl ether contained considerable amounts of the p-methoxybenzyl ester of 7-phenylacetamidodesacetoxy cephalosporanic acid.

Having now fully described this invention, it will be apparent to one of ordinary skill in the art that many changes and modifications can be made thereto without departing from the spirit or scope of the invention as set forth herein.

What is claimed as new and intended to be covered by Letters Patent is:

1. A process for producing a desacetoxy cephalosporanic acid represented by formula (III),

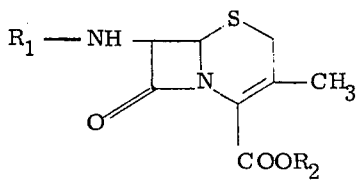

(III)

wherein $R_1$ is acyl, selected from the group consisting of 2-phenylacetyl, phenoxyacetyl, 2-phenoxybutyryl, 2-carboxy-2-phenylacetyl, 2,6-dimethoxybenzoyl, 2-ethoxy-1-naphthoyl, 2-sulfo-2-phenylacetyl, 2-azido-2-phenylacetyl, 2-thienylacetyl, 2-amino-2-phenylacetyl, and $R_2$ is alkyl selected from the group consisting of t-butyl and 2,2,2-trichloroethyl or arylalkyl selected from the group consisting of benzyl, p-methoxybenzyl, p-nitrobenzyl, benzhydryl, trityl and phenacyl consisting essentially of heating a penicillin sulfoxide of the formula (I),

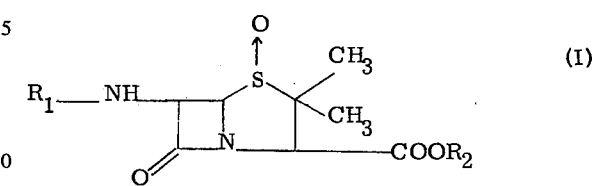

(I)

wherein $R_1$ and $R_2$ are the same as hereinbefore defined, at 80° to 130°C for at least one hour in an inert organic solvent selected from the group consisting of 1,4-dioxane, n-propyl ether, methyl n-propyl ketone, methyl isobutyl ketone, ethyl carbonate, n-propyl acetate, 1,2-dichloropropane and 1,1,2-trichloroethane in the presence of 0.1 to 4 mole per one mole of said penicillin sulfoxide of a sulfonate represented by formula (VI),

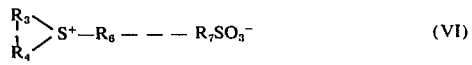

(VI)

wherein $R_3$, $R_4$ and $R_6$ are lower alkyl, phenyl, benzyl, phenylethyl, $R_7$ is 1-12C alkyl, phenyl 1-12C alkyl-substituted phenyl, naphthyl, 1-12C alkyl-substituted naphthyl, halogen-substituted phenyl, and wherein $R_3$ and $R_4$ may bond to form a 4-5C heterocyclic polymethylene ring and $R_6$ and $R_7$ may bond to form a polymethylene link and wherein the sulfonate anion of said compound is selected from the group consisting of methanesulfonate, ethanesulfonate, propanesulfonate, benzenesulfonate, p-toluenesulfonate, trimethylbenzenesulfonate, dodecylbenzenesulfonate, chlorobenzenesulfonate and naphthalenesulfonate.

2. A process for producing a desacetoxy cephalosporanic acid represented by formula (III),

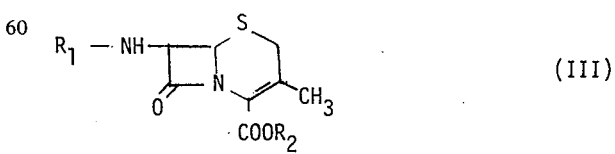

(III)

wherein $R_1$ is acyl, selected from the group consisting of 2-phenylacetyl, phenoxyacetyl, 2-phenoxybutyryl, 2-carboxy-2-phenylacetyl, 2,6-dimethoxy benzoyl, 2- ethoxy-1-maphthoyl, 2-sulfo-2-phenylbutyryl, 2-azido-2-phenylacetyl, 2-thienylacetyl, 2-amino-2-phenylacetyl, and R₂ is alkyl selected from the group consisting of t-butyl and 2,2,2-trichloroethyl or arylalkyl selected from the group consisting of benzyl, p-methoxybenzyl, p-nitrobenzyl, benzhydryl, trityl and phenacyl consisting essentially of heating a penicillin sulfoxide of the formula (I),

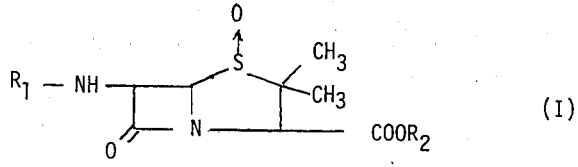

(I)

wherein R₁ and R₂ are the same as hereinbefore defined in the presence of 0.2 to 4 mole of an S,S,S-trimethylsulfoxonium sulfonate represented by the formula (VII),

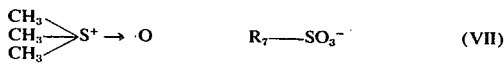

(VII)

wherein R₇ is 1-12C alkyl, phenyl, 1-12C alkyl-substituted phenyl, naphthyl, 1-12C alkyl-substituted naphthyl, or halogen-substituted phenyl at 95° to 120°C for at least one hour in an inert organic solvent selected from the group consisting of 1,4-dioxane, methyl isobutyl ketone, 1,2-dichloropropane, 1,1,2-trichloroethane, n-propyl ether, methyl n-propyl ketone, ethyl carbonate and n-propyl acetate.

3. A process for producing a desacetoxy cephalosporanic acid represented by the formula (III),

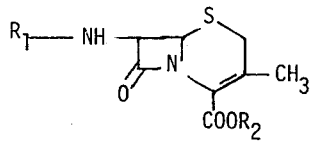

wherein R₁ is acyl, selected from the group consisting of 2-phenylacetyl, phenoxyacetyl, 2-phenoxybutyryl, 2-carboxy-2-phenylacetyl, 2,6-dimethoxybenzoyl, 2-ethoxy-1-naphthoyl, 2-sulfo-2-phenylacetyl, 2-azido-2-phenylacetyl, 2-thienylacetyl, and 2-amino-2-phenylacetyl and R₂ is alkyl selected from the group consisting of t-butyl and 2,2,2-trichloroethyl or arylalkyl selected from the group consisting of benzyl, p-methoxybenzyl, p-nitrobenzyl, benzhydryl, trityl and phenacyl consisting essentially of heating a penicillin sulfoxide of the formula (I),

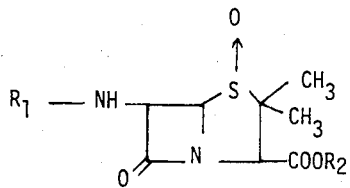

wherein R₁ and R₂ are the same as hereinbefore defined, at 50° to 160°C in an inert organic solvent selected from the group consisting of 1,4-dioxane, n-propyl ether, methyl n-propyl ketone, methyl isobutyl ketone, ethyl carbonate, n-propyl acetate, 1,2-dichloropropane and 1,1,2-trichloroethane in the presence of 0.1 to 4 mole per one mole of said penicillin sulfoxide of a sulfonate represented by the formula (II),

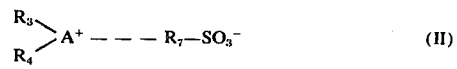

(II)

wherein A is S—R₆ or CH₃—S → O and R₃, R₄ and R₆ are lower alkyl, phenyl, benzyl or phenethyl, R₇ is 1-12C alkyl, phenyl, 1-12C alkyl-substituted phenyl, naphthyl, 1-12C alkyl-substituted naphthyl, halogen-substituted phenyl, and wherein when A is S—R₆, R₃ and R₄ may bond to form a 4-5C heterocyclic polymethylene ring and R₆ and R₇ may bond to form a polymethylene link selected from the group consisting of S,S,S-trimethylsulfonium sulfonate, S,S-diethyl-S-methylsulfonium sulfonate, S,S-dipropyl-S-methylsulfonium sulfonate, S,S-dibutyl-S-methylsulfonium sulfonate, S,S,S-triethylsulfonium sulfonate, S,S-dimethyl-S-benzylsulfonium sulfonate, S,S-diethyl-S-benzylsulfonium sulfonate, S,S-dipropyl-S-benzylsulfonium sulfonate, S,S-dibutyl-S-benzylsulfonium sulfonate, S,S-dimethyl-S-phenethylsulfonium sulfonate, S-methyl-S,S-dibenzylsulfonium sulfonate, S-ethyl-S,S-dibenzylsufonium sulfonate, S-methyl-S,S-bisphenethylsulfonium sulfonate, S-ethyl-S,S-bisphenethylsulfonium sulfonate, S-methyltetrahydrothiophenium sulfonate, S-ethyltetrahydrothiophenium sulfonate, S-benzyltetrahydrothiophenium sulfonate, S-phenethyltetrahydrothiophenium sulfonate, S-methyltetrahydrothiopyranium sulfonate, and S-ethyltetrahydrothiopyranium sulfonate wherein the sulfonate anion is a compound selected from the group consisting of methane sulfonate, ethane sulfonate, propane sulfonate, benzene sulfonate, p-toluene sulfonate, trimethylbenzene sulfonate, dodecylbenzene sulfonate, p-chlorobenzenesulfonate, naphthalenesulfonate, S,S-diethyl(3-sulfopropyl)-sulfonium hydroxide, S,S-dibenzyl(3sulfopropyl)-sulfonium hydroxide, and 3-sulfopropyltetrahydrothiophenium hydroxide.

4. The process of claim 1, wherein the sulfonate is a compound selected from the group consisting of S,S,S-tri-lower alkylsulfonium, S,S-dilower alkyl-S-benzylsulfonium, S,S-dilower alkyl-S-phenetylsulfonium, S-lower alkyl-S,S-dibenzylsulfonium, S-lower alkyl-S,S-bis-phenetylsulfonium, S-lower alkyltetrahydrothiophenium, S-benzyltetrahydrothiophenium, S-phenethyltetrahydrothiophenium and S-lower alkyltetrahydrothiopyranium sulfonate.

5. The process of claim 1, wherein the sulfonate is selected from the group consisting of S,S,S-trimethylsulfonium sulfonate, S,S-diethyl S-methylsulfonium sulfonate, S,S-dipropyl S-methylsulfonium sulfonate, S,S-dimethyl S-benzylsulfonium sulfonate, S,S-diethyl S-benzylsulfonium sulfonate, S,S-dibenzyl S-methylsulfonium sulfonate, S-methyltetrahydrothiophenium sulfonate, S-ethyltetrahydrothiophenium sulfonate, S-benzyltetrahydrothiophenium sulfonate and S-methyltetrahydrothiopyranium sulfonate.

6. The process of claim 5, wherein the sulfonate anion of said sulfonate is selected from the group consisting of methanesulfonate, ethanesulfonate and p-toluenesulfonate.

7. The process of claim 6, wherein the inert organic solvent is selected from the group consisting of 1,4- dioxane, methyl isobutyl ketone, 1,2-dichloropropane and 1,1,2-trichloroethane.

8. The process of claim 1, wherein the sulfonate is selected from the group consisting of the inner salt of S,S-diethyl (3-sulfopropyl)sulfonium hydroxide, the inner salt of S,S-dibenzyl(3-sulfopropyl)sulfonium hydroxide and the inner salt of 3-sulfopropyltetrahydrothiophenium hydroxide.

9. The process of claim 1, wherein the inert organic solvent is selected from the group consisting of 1,4-dioxane, methyl isobutyl ketone, 1,2-dichloropropane, 1,1,2-trichloroethane and the sulfonate is selected from the group consisting of S,S,S-trimethylsulfonium methanesulfonate, S,S-diethyl-S-methylsulfonium p-toluenesulfonate, and S-methyltetrahydrothiophenium p-toluenesulfonate.

10. The process of claim 9, wherein the amount of the sulfonate is 0.5 to 4 mole per one mole of the penicillin sulfoxide, and said heating is conducted at a temperature of 90° to 115°C.

11. The process of claim 2, wherein the sulfonate anion of the S,S,S-trimethylsulfoxonium sulfonate is selected from the group consisting of methanesulfonate, ethanesulfonate, propanesulfonate, butanesulfonate, benzenesulfonate, dimethylbenzenesulfonate, trimethylbenzenesulfonate and alkylbenzenesulfonate.

12. The process of claim 2, wherein the inert organic solvent is selected from the group consisting of 1,4-dioxane, methylisobutylketone, 1,2-dichloropropane and 1,1,2-trichloroethane.

13. The process of claim 2, wherein the sulfonate anion of the S,S,S-trimethylsulfoxonium sulfonate is selected from the group consisting of methanesulfonate, ethanesulfonate, benzenesulfonate, trimethylbenzenesulfonate, p-toluenesulfonate and dodecylbenzenesulfonate and wherein the inert organic solvent is 1,1,2-trichloroethane.

14. The process of claim 13 wherein the amount of S,S,S-trimethylsulfoxonium sulfonate is 0.5 to 4 mole per one mole of penicillin sulfoxide, and wherein said heating is conducted at the reflux temperatures of said inert organic solvent.

* * * * *